(12) United States Patent
Burstein et al.

(10) Patent No.: US 8,303,664 B1
(45) Date of Patent: Nov. 6, 2012

(54) JOINT REPLACEMENT SPACERS

(76) Inventors: Albert H. Burstein, Reno, NV (US); Jonathan T. Deland, New York, NY (US)

(*) Notice: Subject to any disclaimer, the term of this patent is extended or adjusted under 35 U.S.C. 154(b) by 0 days.

(21) Appl. No.: 13/332,662

(22) Filed: Dec. 21, 2011

(51) Int. Cl.
*A61F 2/30* (2006.01)

(52) U.S. Cl. ........ 623/18.11; 623/20.11; 623/20.14; 623/20.21; 623/21.11; 623/21.15

(58) Field of Classification Search .......... 623/14.12, 623/20.16, 20.26, 20.33, 20.35, 21.11, 21.14, 623/21.15, 21.19, 22.43, 23.6, 18.11
See application file for complete search history.

(56) References Cited

U.S. PATENT DOCUMENTS

| | | | |
|---|---|---|---|
| 4,863,474 A | 9/1989 | Brown et al. | |
| 4,964,865 A * | 10/1990 | Burkhead et al. | 623/19.11 |
| 7,160,329 B2 | 1/2007 | Cooney, III et al. | |
| 7,628,819 B2 | 12/2009 | Gupta et al. | |
| 7,758,581 B2 | 7/2010 | Chervitz et al. | |
| 7,837,739 B2 | 11/2010 | Ogilvie | |
| 7,909,883 B2 | 3/2011 | Sidebotham | |
| 7,963,968 B2 | 6/2011 | Dees, Jr. | |
| 2006/0069446 A1 | 3/2006 | Ragusa et al. | |
| 2007/0233251 A1 | 10/2007 | Abdou | |
| 2007/0233269 A1 | 10/2007 | Steines et al. | |
| 2009/0234453 A1 | 9/2009 | Steinberg | |
| 2009/0234454 A1 | 9/2009 | Siegal | |
| 2010/0262254 A1 | 10/2010 | Lawrence et al. | |
| 2011/0054628 A1 | 3/2011 | Banks et al. | |

FOREIGN PATENT DOCUMENTS

| | | |
|---|---|---|
| AU | 2004201647 A1 | 2/2005 |
| DE | 10130796 A1 | 1/2003 |
| EP | 1637095 A2 | 3/2006 |
| FR | 2465470 A1 | 3/1981 |
| FR | 2709948 A1 | 3/1995 |
| WO | 2011071782 A1 | 6/2011 |

\* cited by examiner

*Primary Examiner* — Bruce E Snow
*Assistant Examiner* — Brian Dukert
(74) *Attorney, Agent, or Firm* — Peter K. Sollins; Foley Hoag LLP (57) ABSTRACT

Joint replacement spacers that fully seat against the cut surface of a bone while remaining free to move on the cut surface within prescribed limits; methods of joint replacement using such spacers.

24 Claims, 14 Drawing Sheets

SECTION A-A

JOINT REPLACEMENT SPACERS

SUMMARY

Devices and methods are disclosed for joint replacement.

DETAILED DESCRIPTION

A spacer for joint replacement can be used to replace a portion of bone in a joint. The joint is originally formed by two bones, each having a cartilaginous articulating surface. The joint schematically shown in FIG. 1 includes a first bone 101 with an articular surface 102 meeting a second bone 103 with an articular surface 104. The cartilage is not drawn separately for simplicity, but is meant to be included in each schematically drawn bone. Under various circumstances, a patient may require replacement of the articular surface (and possibly underlying bone) of one bone, even though the second bone remains healthy. A joint replacement spacer can be designed so that it replaces only the diseased portion of the first bone, leaving more healthy bone intact than would a full joint replacement. The joint replacement spacer can be designed to interact with the natural articular surface of the second bone, or else to articulate with a prepared surface of the second bone.

Figure 1:
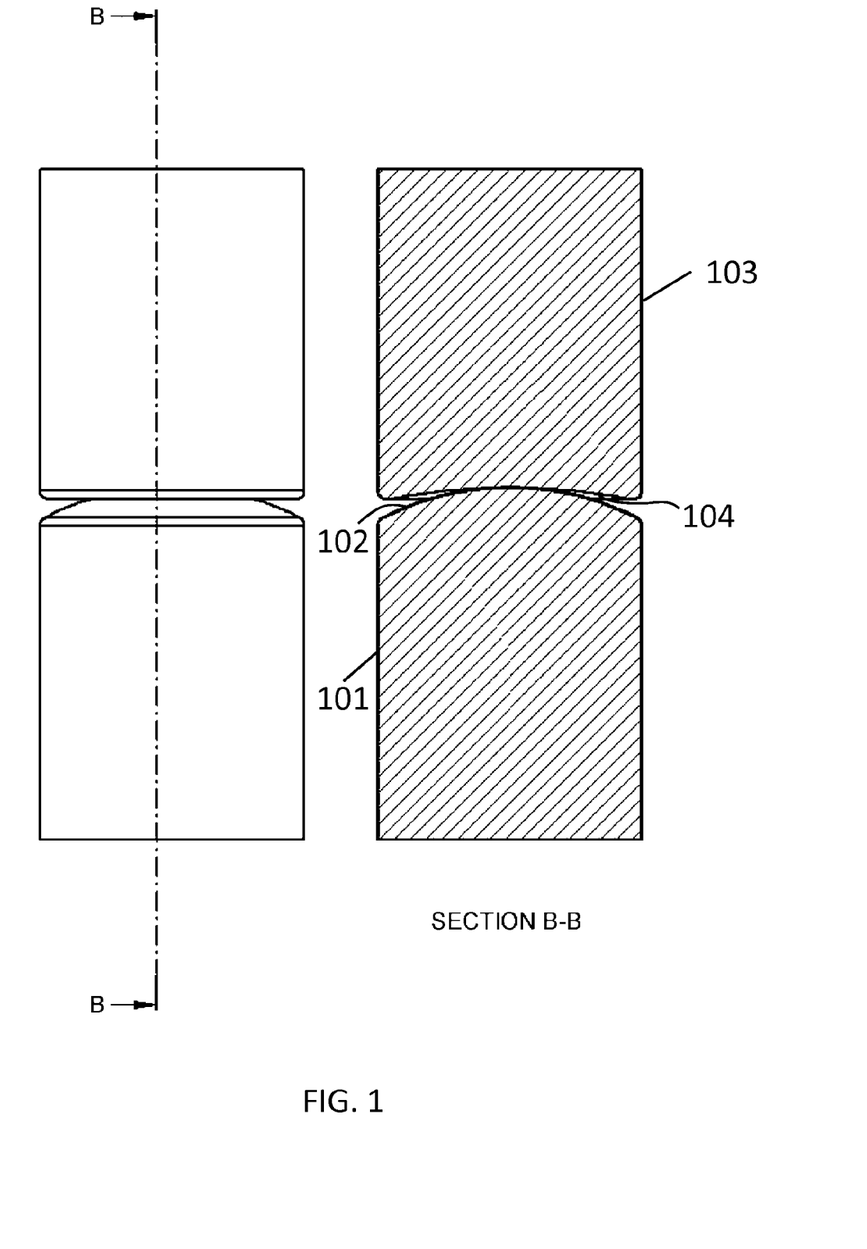
FIG. 1 schematically shows a joint in a patient, prior to placement of a joint replacement spacer.

One method of joint replacement is as follows:

First, as in FIG. 1, a surgeon distracts the joint to reveal the articular surface and the portion of the first bone to be replaced, as well as the articular surface of the second, healthy bone.

Figure 2:
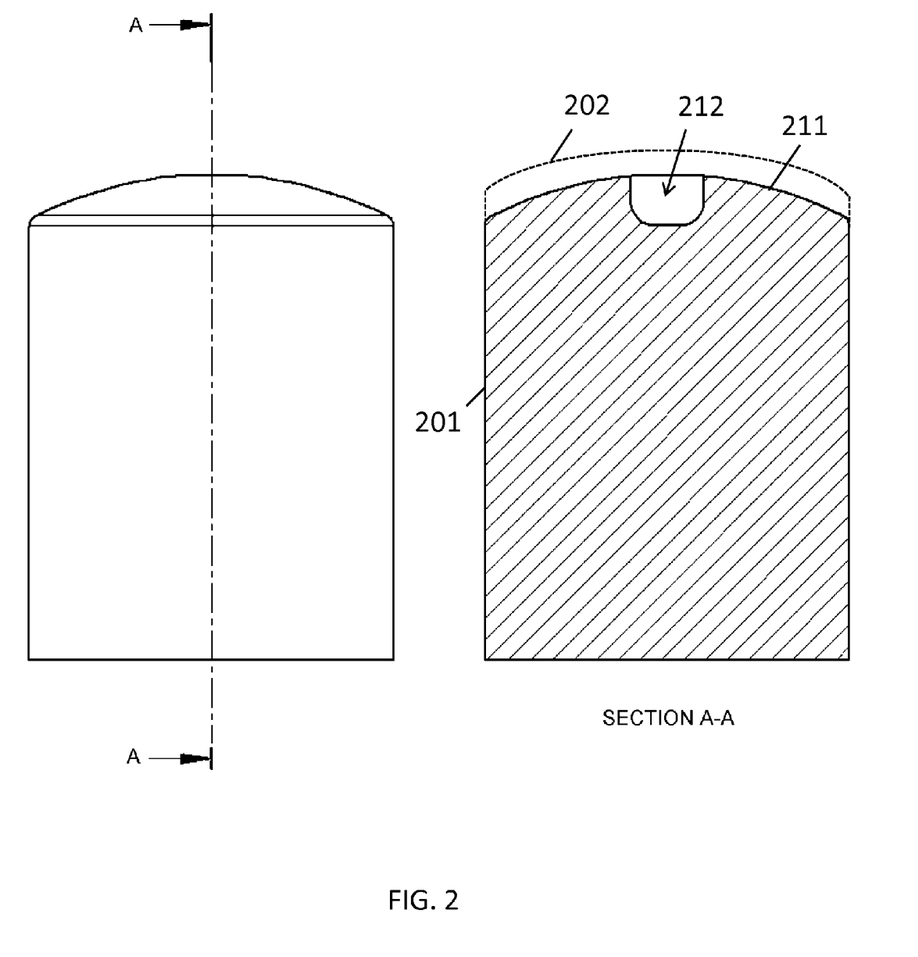
FIG. 2 schematically shows one bone in the joint having been prepared for a joint replacement spacer by removing the articulating surface of the bone to form a cut surface and a cavity.

The first bone 201 is then prepared for replacement, as schematically shown in FIG. 2, by (a) removing the articular surface 202 of the first bone, thereby creating a cut surface 211 on the first bone 201, and (b) forming a cavity 212 in the first bone 201, so that the cavity 212 opens onto the cut surface 211. Forming the cut surface 211 and forming the cavity 212 can be done serially, in either order. The entire articular surface 202 can be removed and the cut surface 211 created before the cavity 212 is formed, with the benefit that it may be easier to achieve a precise depth of the cavity 212 below the cut surface 211. Or the cavity 212 can be formed before the cut surface 211 is created, allowing any bone fragments or splinters generated while forming the cavity 212 to be removed along with the articular surface 202 of the first bone 201. Another alternative is to form both the cavity 212 and cut surface 211 simultaneously in a single step, for example with a specialized bone-cutting tool.

Figure 3:
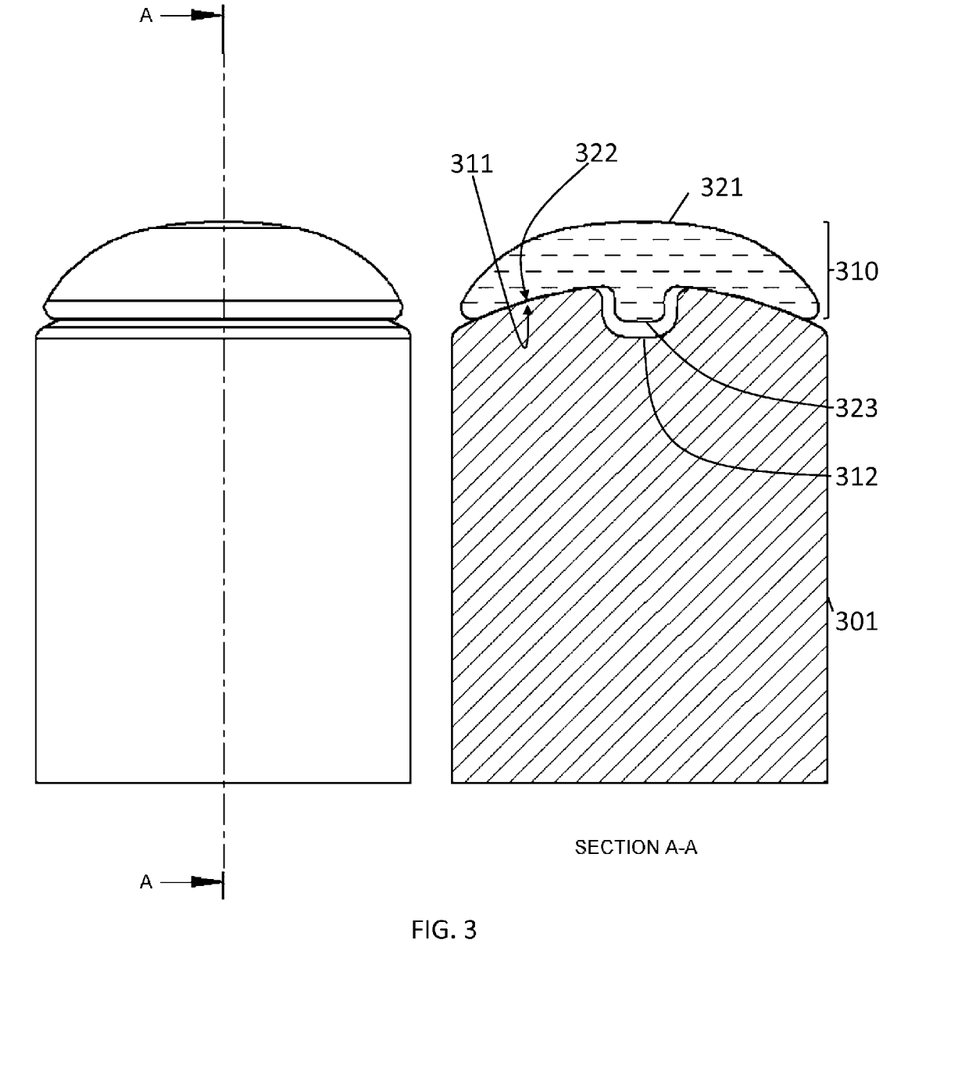
FIG. 3 schematically shows the prepared bone with a spacer seated on the cut surface.

Once the first bone is prepared, the spacer 310 can be placed on the cut surface 311, as schematically shown in FIG. 3. The spacer 310 typically has a primary surface 321 for (a) replacing the articular surface of the first bone 301 and (b) articulating with the second bone. The spacer also typically has a secondary surface 322 that is placed against the cut surface 311 of the first bone 301. The secondary surface 322 and the cut surface 311 are shaped and sized relative to each other so that the secondary surface 322 can fully seat against the cut surface 311 while remaining free to move on the cut surface 311.

Figure 4:
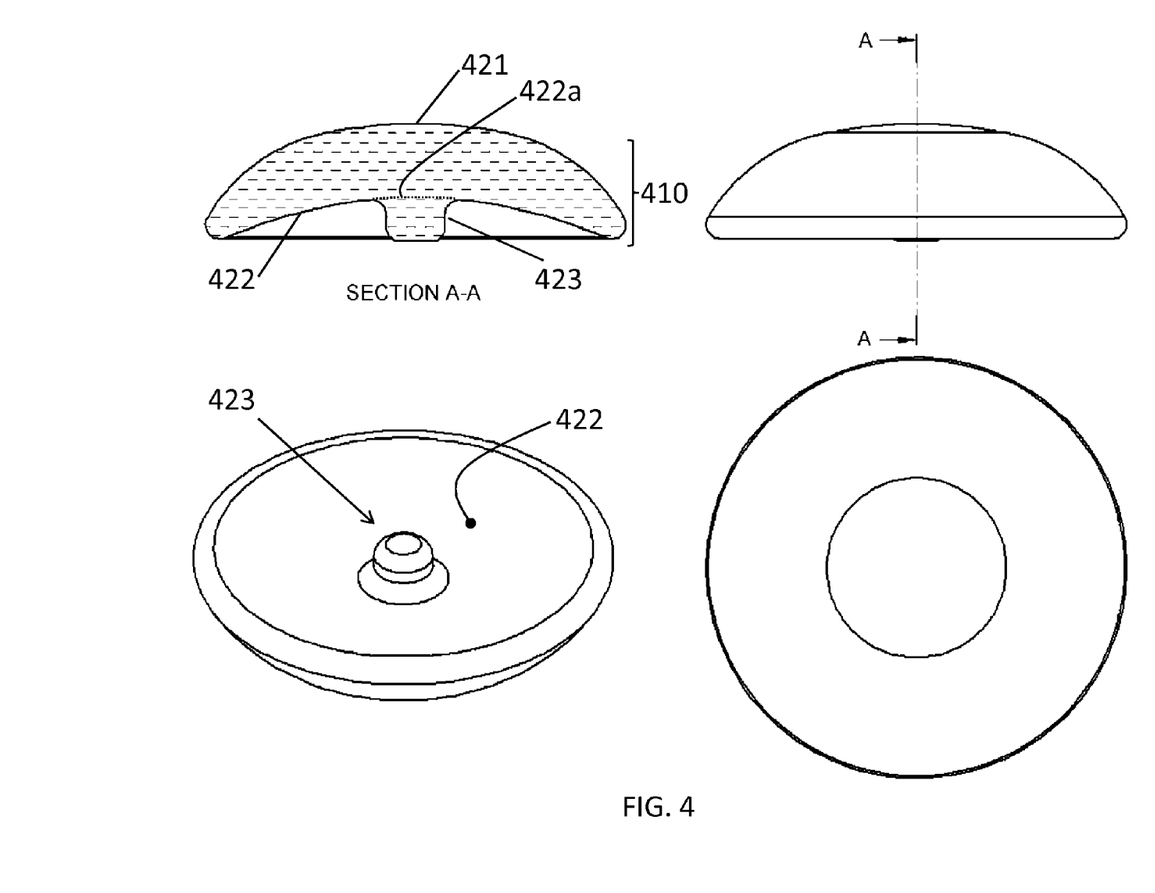
FIG. 4 schematically shows various views of a spacer with a spherical secondary surface.

One example of such a spacer 410 is schematically shown in FIG. 4. In this particular example, the secondary surface 422 defines a portion of a sphere. The spacer 310 also typically includes a bump 323 that is sized and shaped relative to the cavity 312 so that the bump 323 is capable of moving "laterally" within the cavity 312, even when the joint is under load. (The "lateral" direction is described more fully below.) When the secondary surface 322 is fully seated on the cut surface 311, the secondary surface 322 is then free to move on the cut surface 311 to the extent that the bump 323 can move within the cavity 312. Such motion is allowed even when the joint is under load.

The bump allows controlled relative motion between the joint spacer and the cut surface of the bone without the need for stem-like fixation devices. The bumps protrude into the cut joint surface only superficially by design; they allow load and motion to be transferred to the joint surface, rather than to deeper bone. Surface bone is better-adapted than deeper bone for supporting load and motion. Moreover, the low-profile bumps avoid creating large bending stresses on the loaded bone that result from transmitting the load along a stem.

Prior joint replacements typically seek to minimize motion of the spacer against bone when joint is under load. The spacers are specifically designed to maximize motion of the spacer within prescribed limits as described herein.

In some cases, the spacer will include more than one bump, and preparing the first bone will similarly include preparing a number of cavities equal to the number of bumps on the spacer. The bumps may or may not all have the same shape, and the cavities likewise may all have the same shape or may have different shapes.

Figure 5:
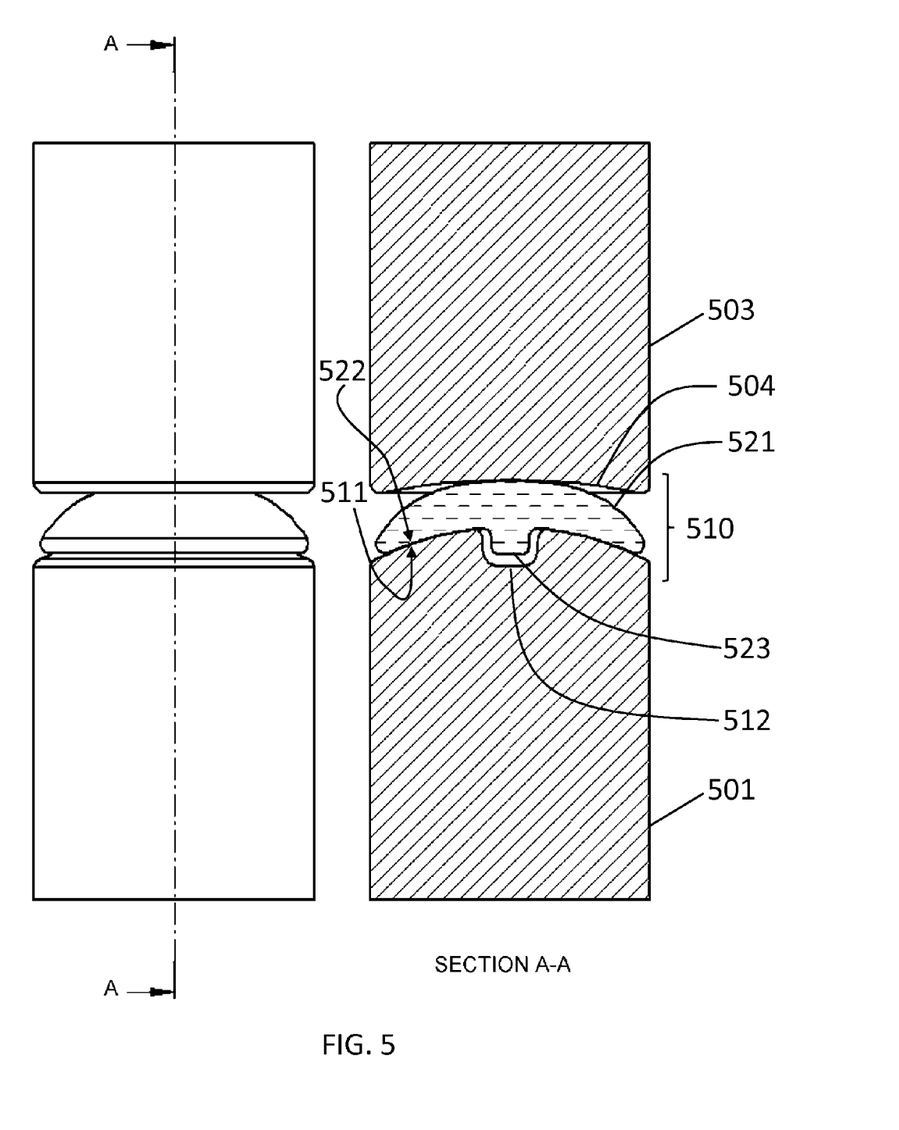
FIG. 5 schematically shows the joint reapproximated with the spacer in place on the cut surface.

FIG. 5 schematically shows the joint reapproximated after placing the spacer 510 on the cut surface 511, so that the primary surface 521 articulates with the articular surface 504 of the second bone 503, and the secondary surface 522 fully seats against the cut surface 511 of the first bone 501. The primary surface 521 of the spacer 510 and the articulating surface 504 of the second bone 503 are generally similar in shape, but will often not be perfectly congruent. For example, in the case of curved surfaces, the radius of curvature of the primary surface 521 of the spacer 510 can be from about 90% to nearly 100% of the radius of curvature of the articulating surface 504 of the second bone 503. For surfaces that cannot be defined by a single radius of curvature, the difference between the primary and articulating surfaces can also be small but non-zero.

The "lateral" directions (i.e. the directions in which the bump 523 is allowed to move within the cavity 512) are defined by the orientation of the secondary surface 511 near the bump 512. For example, FIG. 4 schematically shows that, where the secondary surface 422 approaches the bump 423, one could interpolate an imaginary secondary surface 422a continuing uninterrupted by the bump 423. "Lateral" means any direction that is substantially tangent to (a) a part of the secondary surface 422 near the bump 423, or (b) the imaginary, uninterrupted secondary surface 422a that would exist if the bump 423 were not present. As in FIGS. 5 and 7, any such lateral direction will typically be substantially perpendicular to the depth of the cavity 512 when the spacer 510 is fully seated on the cut surface 511. The direction of the depth of the cavity 523, perpendicular to the lateral directions, will generally be referred to herein as "vertical."

Figure 6:
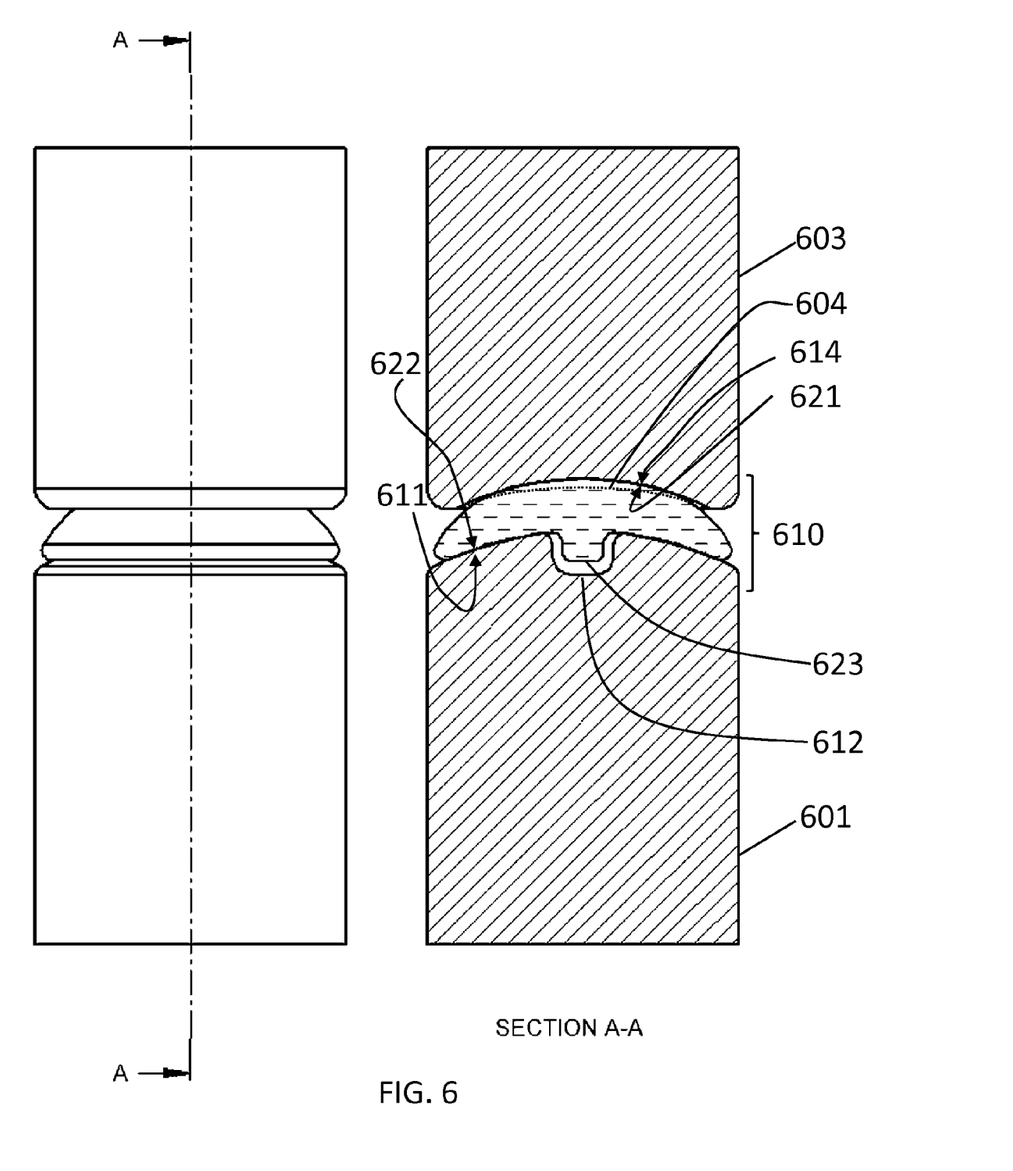
FIG. 6 schematically shows a spacer and a reapproximated joint, wherein the articular surface of the second bone has been removed or reshaped to engage with the primary surface of the spacer.

An additional layer may be provided between the secondary surface of the spacer and the cut surface against which it lies. The additional layer may include a material to promote bone or cartilage growth or act as a shock absorber. Exemplary materials include matrices and hydrogels, possibly seeded with small molecules or biologics. The additional layer may serve as a sustained-release source for a substance eluted into the joint. The additional layer may be deposited on the secondary surface of the spacer or to the cut surface (i.e., by spraying or painting) or may be a discrete object, such as a "washer" or other thin layer that is slipped in between the secondary surface and the cut surface before the joint is reapproximated. As schematically shown in FIG. 6, in some cases the method may include preparing the second bone 603 by removing the second articular surface 604 so as to create a prepared articular surface 614 on the second bone 604. In such cases, when the joint is reapproximated, the primary surface 621 articulates with the prepared articular surface 614 of the second bone 603 rather than the original, second articular surface 604 of the second bone 603. Removing the original, second articular surface 604 of the second bone 603 can be advantageous if the primary surface 621 of the spacer 610 differs in shape from the original articular surface of the first bone 601.

The above methods may be used in essentially any synovial joint (i.e., diarthrosis) in the body, particularly in the smaller joints, such as in the extremeties. Examples of suitable joints in the hand and/or wrist include the carpometacarpal joint of the thumb, the scapho-trapezio-trapezoid (STT), the metacarpal-phalangeal joint of the thumb, and the proximal interphalangeal joints. Examples of joints in the foot include the tibiotalar, talonavicular, metatarsal phalangeal, metatarsal tarsal, navicularcuneiform, calcaneal cuboid, subtalar, and interphalangeal (distal and proximal) joints. Joints in the elbow and shoulder may also be well-suited to use of the present spacers and methods.

More generally, as schematically shown in FIG. 4, a spacer 410, for (a) replacing a portion of a first bone, the first bone having a cut surface and a cavity that opens onto the cut surface, and (b) articulating with a second bone, may have a primary surface 421 sized and shaped to articulate with an articular surface of the second bone, a secondary surface 422 sized and shaped to conform to the cut surface of the first bone, so that the spacer 410 tends to remain fully seated against the cut surface while remaining free to move on the cut surface, and a bump 423 protruding from the secondary surface sized, shaped and located such that, when the secondary surface is fully seated against the cut surface, the bump extends into the cavity, without laterally filling the cavity, thereby leaving the spacer free to move on the cut surface to the extent that the bump can move laterally within the cavity, even when the joint is under load.

The spacer 410 can be made of a variety of materials, including pyrolytic carbon. In particular, the primary and secondary surfaces and the bump may be formed entirely from pyrolytic carbon. The advantages of the claimed method and the associated spacer are especially well realized when the spacer has pyrolytic carbon surface(s). Pyrolytic carbon has been used as an implant material for several decades in artificial heart valves and artificial joint implants. When used within a joint, the material exhibits extreme biocompatibility, surpassing common implant metals such as stainless steels, titanium alloys, ceramics other than pyrolytic carbon, and cobalt chrome alloys. This extreme biocompatibility allows the body to act in two advantageous ways. First, pyrolytic carbon can transmit sliding motion under load to synovial joint surfaces while allowing the surfaces to remain healthy and functional over prolonged periods of time. Its biocompatibility against articular cartilage clinically surpasses all presently-known common implant metals. This property provides prolonged load bearing contact between the joint spacer and the remaining cartilage surface. The second advantage of pyrolytic carbon is its reaction in the presence of newly formed bone surfaces, such as are created when the end of a diseased bone is resected. In this case, pyrolytic carbon appears to encourage the formation of a new load transfer surface that responds favorably to small induced motions while transmitting joint loads. This property leads to the advantageous element of the claimed joint spacer, namely the absence of the need for rigid fixation between the spacer and the bone.

Figure 7:
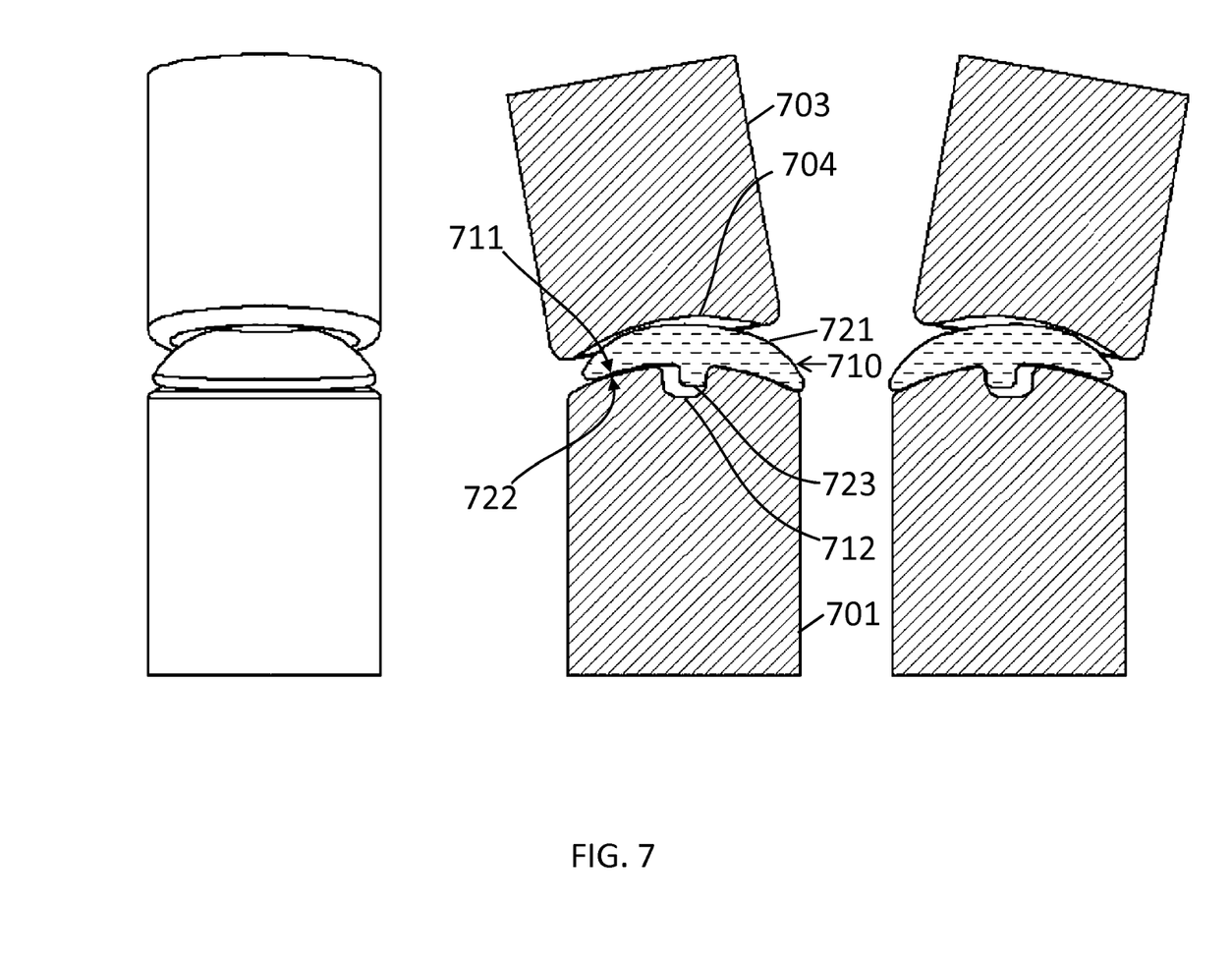
FIG. 7 schematically shows a spacer translating when the joint is under load.

FIG. 7 schematically shows a spacer 710 translating in a reapproximated joint, when the joint is under load. As the joint bends, the spacer is free to translate laterally until the bump 723 meets the cavity wall 712. In some joints, as in FIG. 7, flexing may cause the spacer to translate toward the obtuse-angled outside of the joint, while extension may cause the spacer to translate toward the acute-angled inside of the joint. In other joints, the flexing may cause the spacer to move to the inside, while extension may cause the spacer to move to the outside.

Figure 8:
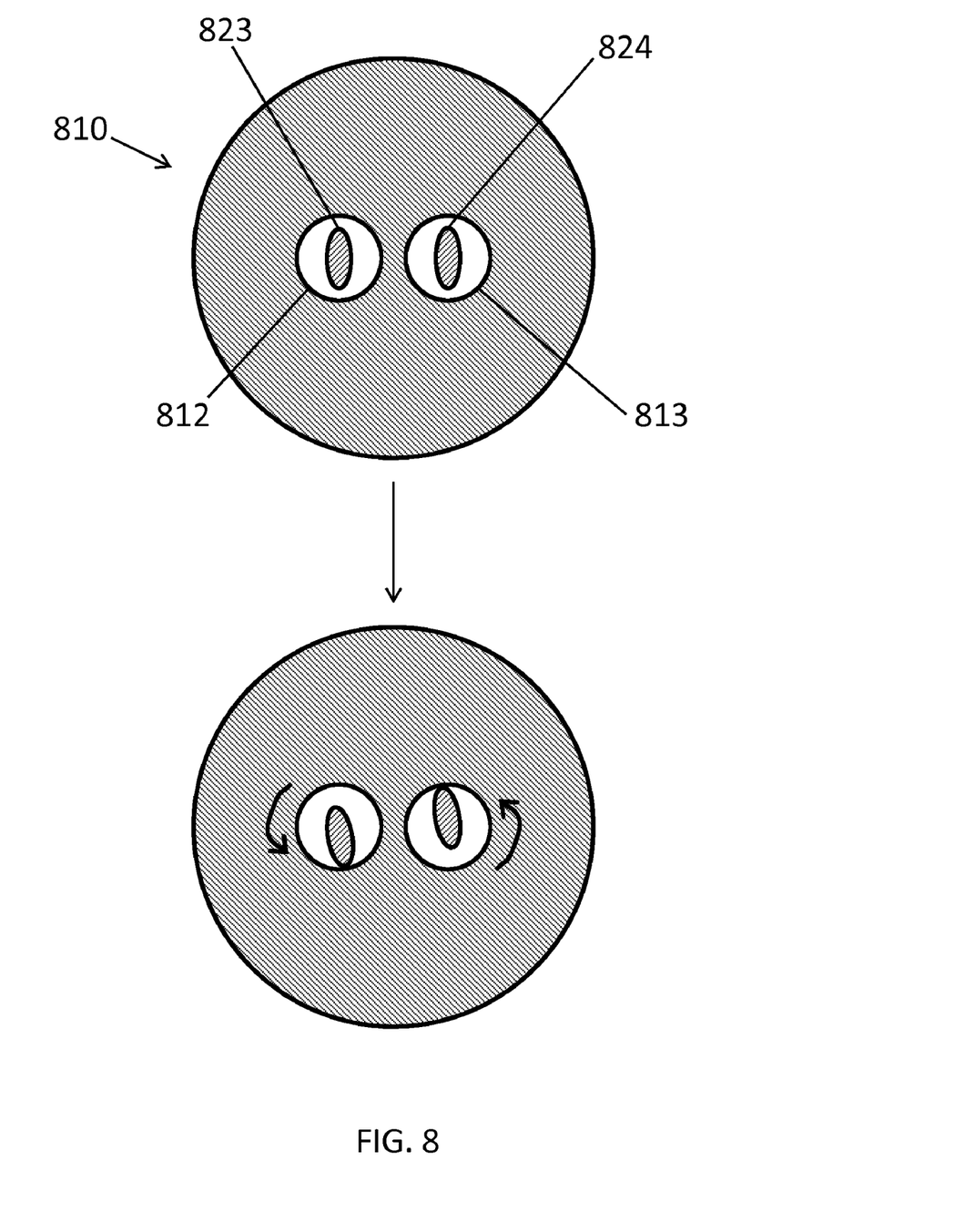
FIG. 8 schematically shows rotation of a spacer on the cut surface.

FIG. 8 schematically shows a cross-section of a spacer with two bumps 823, 824 extending into two prepared cavities 812, 813. In this case, the bumps 823, 824 have elliptical lateral cross-sections. As the spacer rotates, each bump 823, 824 is free to move within its cavity 812, 813, traveling in opposite directions, until the two bumps 823, 824 reach the walls of the cavity 812, 813. In this way, the relative size and shape of the bumps 823, 824 and cavities 812, 813 can limit rotation of the spacer 810 relative to the first bone 801. A spacer with only a single bump extending into a single cavity can also be designed to rotate freely up to a limit. For example, the lateral cross-sectional shapes of the bump and spacer are could be ellipses with equal eccentricity. As long as the major axis of the bump is smaller than the major axis of the cavity and larger than the minor axis of the cavity, then the bump will be free to rotate within the cavity within a limited range.

Figure 9A:
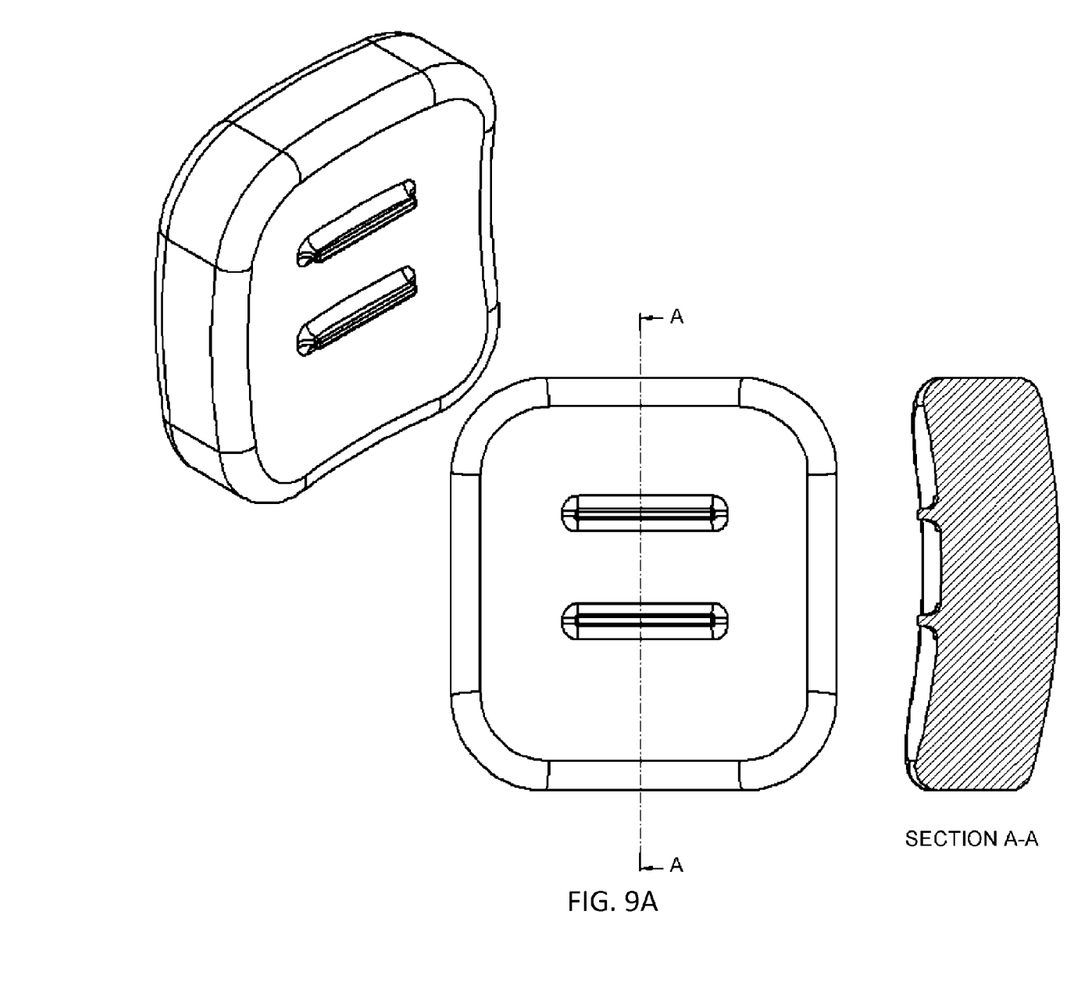
FIGS. 9A-B schematically show spacer shapes.
Figure 9B:
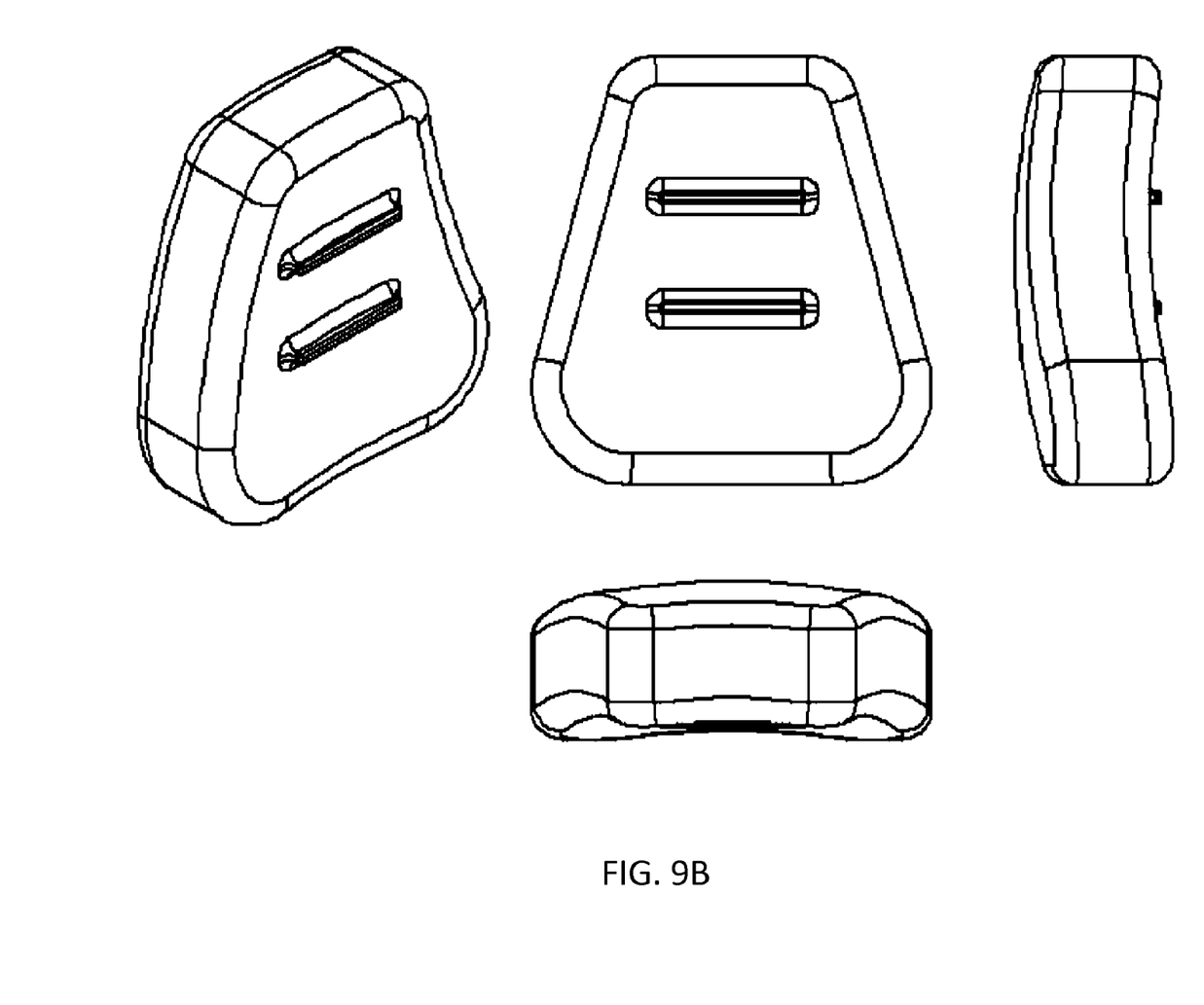

As shown schematically in FIGS. 9A-B, the overall shape of the spacer can be designed to fit a variety of different joints. Spacers can be partially cylindrical, spherical, spheroidal (either oblate or prolate), ellipsoidal, quadrilateral, such as square, rectangular, rhomboidal, or trapezoidal, for example. Corners may be rounded.

Figure 11:
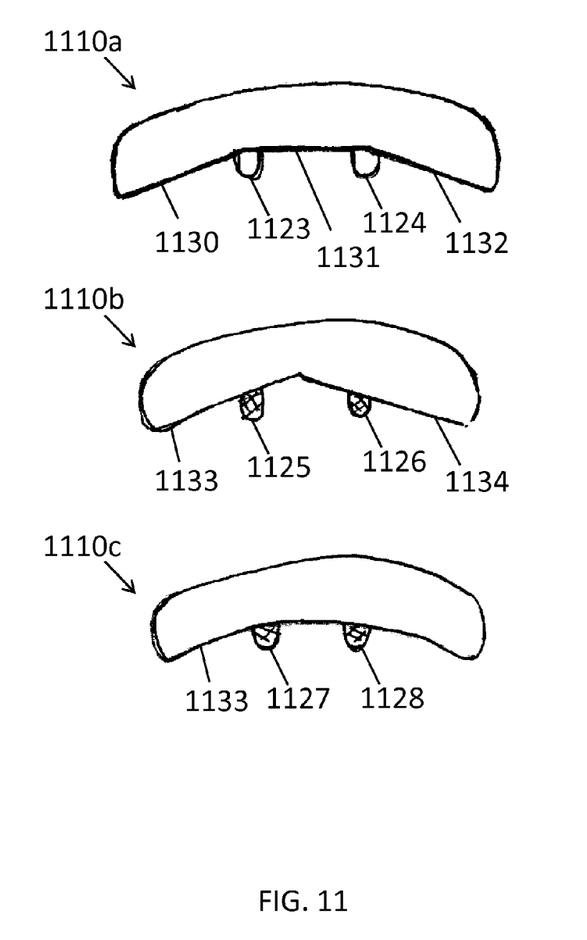
FIG. 11 schematically shows several possible positions of a bump on the secondary surface and several shapes of the secondary surface.

In addition to the various possible shapes of the spacer overall, the secondary surface in particular can have a variety of different shapes, such as cylindrical, spherical, spheroidal (oblate or prolate), and ellipsoidal. Typically the secondary surface will define a portion of one of these shapes. For example, FIG. 4 shows a spacer 410 with a concave, spherical secondary surface 422 interrupted by a single bump 423. The secondary surface 422 may be either concave or convex, depending on the geometry of the joint in question. The secondary surface may include one or more planar portions. The planar portions may lie in planes that are not parallel portions, for example, as shown in FIG. 11, two non-parallel planar portions roughly outlining a chevron, or three non-parallel planar portions roughly outlining a trapezoid. The particular shape of the secondary surface can depend intimately on the shape of the original bones in the joint.

Figure 10:
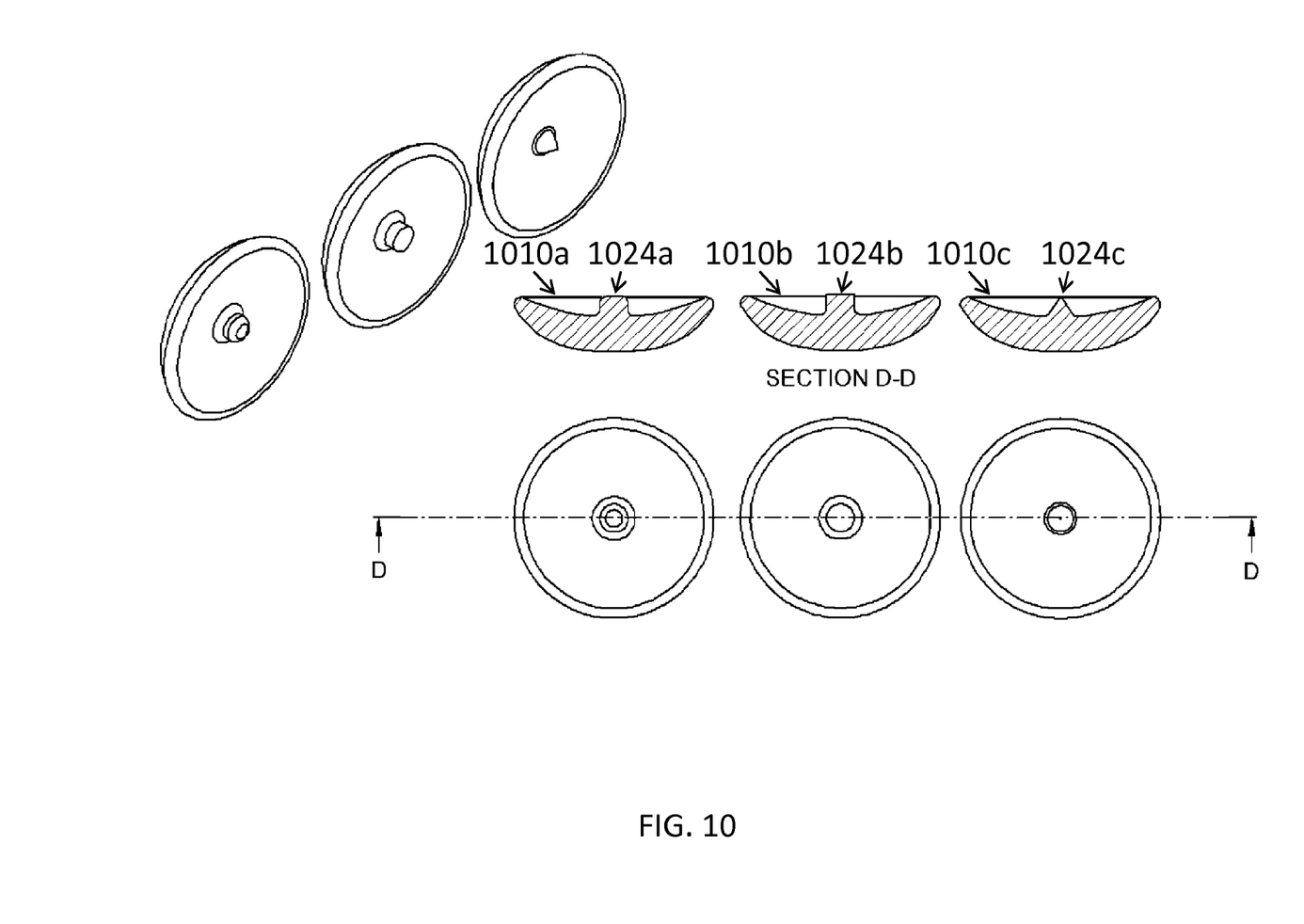
FIG. 10 schematically shows several bump shapes in exemplary spacers.

FIG. 10 schematically shows several bump shapes. Spacers 1010a, 1010b, and 1010c are similar except for their bump shapes, which vary from blunt 1024b to slightly tapered 1024a to substantially tapered 1024c. The corresponding cavity (not shown) for each bump may have a complementary shape to its bump so that, when the secondary surface is fully seated against the cut surface, the bump is able to translate in any lateral direction within the cavity. Or the bump and cavity can be relatively sized and shaped so that, when the secondary surface is fully seated against the cut surface, the bump is able to translate in substantially only a single lateral direction within the cavity. The bump and cavity can also be relatively sized and shaped so that, when the secondary surface is fully seated against the cut surface, the bump is able to rotate about an axis perpendicular to the lateral direction. The relative size and shape of the cavity and the bump may also inhibit or prevent rotational motion, as schematically shown in FIGS. 7 and 8. In all cases, the motion of the bump, translation or rotation or both, can occur even when the joint is under load.

Figure 13A:
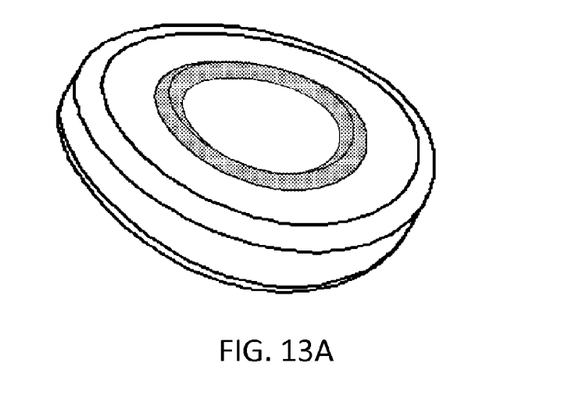
FIGS. 13A-B schematically show spacers having ring-shaped bumps.
Figure 13B:
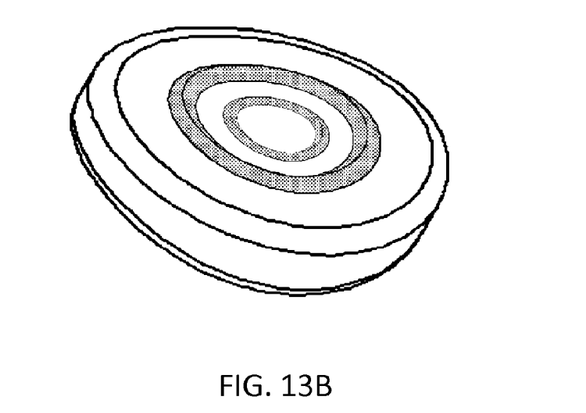

FIG. 11 schematically shows several possible positions of the bump on the secondary surface and several shapes of the secondary surface. A spacer 1110a can have a secondary surface with three planar portions 1130, 1131, 1132 outlining a trapezoidal cross-section. In this case, the two bumps 1123, 1124 extend vertically from the secondary surface, roughly parallel to one another. A spacer 1110b can alternatively have a secondary surface with two planar portions 1133, 1134. Similarly, the two bumps 1125, 1126 extend vertically from the secondary surface, roughly parallel to one another. In another alternative, a spacer 1110c can have a curved secondary surface. Again, the two bumps 1127, 1128 extend vertically from the secondary surface, roughly parallel to one another. Each embodiment in FIG. 11 has two bumps extending parallel to one another. Bumps are typically positioned either so that they run parallel to one another or at right angles to one another. A bump may also be formed as a raised ring (FIG. 13A), and multiple bumps of this shape are typically positioned concentrically to one another (FIG. 13B).

Figure 12:
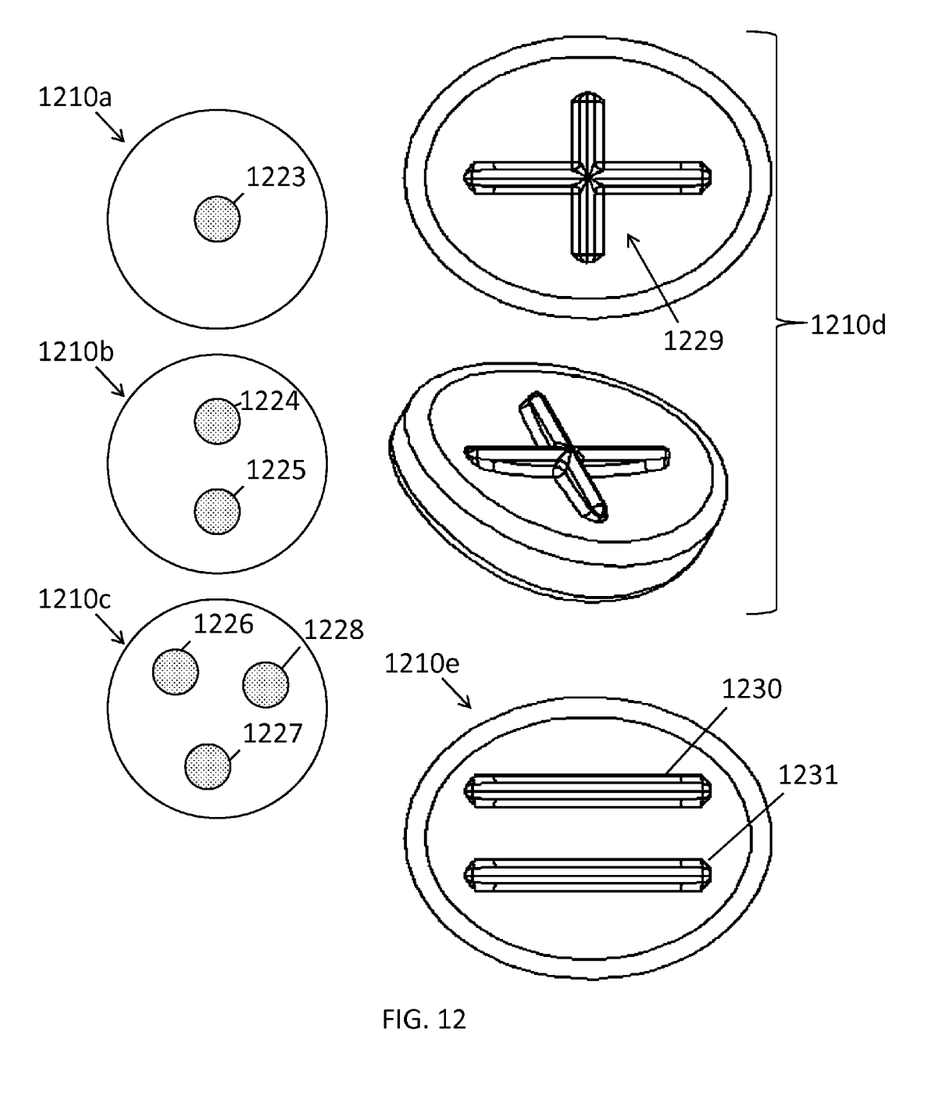
FIG. 12 schematically shows several different arrangements and shapes of bumps on the secondary surface.

FIG. 12 schematically shows several different arrangements and shapes of bumps on the secondary surface. One embodiment of the spacer 1210a has only a single bump 1223 with a generally circular lateral cross-section. Other embodiments 1210b, 1210c have two such bumps 1224, 1225, and three such bumps 1226, 1227, 1228, respectively. Another embodiment of the spacer 1210d has a single bump 1229 formed as a cross. Still another embodiment of the spacer 1210e has two separate, elongated bumps 1230, 1231.

In some cases, the engagement of the secondary surface limits the motion of the spacer on the cut surface in one lateral direction, while the relative size and shape of the bump and cavity limit the motion of the spacer in a different, possibly perpendicular, lateral direction. For example, in the roughly chevron- or trapezoid-shaped embodiments shown in FIG. 11, the relative slopes of the non-parallel planar surfaces can substantially limit the movement of the spacer on the cut surface in one lateral direction. Each planar portion of the secondary surface lies in a different plane, and those planes intersect along lines. The chevron- and trapezoid-shaped embodiments substantially inhibit motion of the spacer on the cut surface perpendicular to the lines of intersection, but they do not substantially inhibit motion parallel to the lines of intersection. The bump and cavity can then be relatively shaped and sized so as to constrain the lateral motion of the spacer parallel to the lines of intersection.

Alternatively, the lateral motion of the bump in the cavity may be constrained, not by the engagement of the secondary surface and cut surface, but rather by the relative shapes and sizes of the bump and the cavity. For example, the bump may be roughly the same size as the cavity in a first lateral direction, but much smaller than the cavity in a different, second lateral direction, possibly perpendicular to the first direction. This arrangement would allow for little to no lateral motion of the bump in the cavity in the first direction, but substantial lateral motion in the second direction.

A lateral cross-section of the bump can define a wide variety of shapes, including for example, shapes that are roughly a polygon, a circle, an ellipse, an oval, or other closed curve. In the case of a bump having a generally polygonal lateral cross-section, the vertices of the polygon will in some cases be rounded over (or filleted in the case of convex shapes), especially if the surfaces are made of pyrocarbon, which typically does not hold a sharp edge. A lateral cross-section of the bump may also define more complicated shapes, like a cross. A lateral cross-section of the cavity can likewise define a wide variety of shapes, just like the bump. In some cases, the lateral cross-sections of the bump and the cavity will define two shapes that are geometrically similar (in the sense that the two shapes are the same except for their size and orientation).

In some cases, the bump and cavity will be sized and shaped relative to one another such that, when the secondary surface is fully seated against the cut surface and the joint is under load, there exists at least one relative position of spacer and bone in which the bump is not in contact with the wall of the cavity. FIGS. 3 and 6, for example, shows a vertical cross-section of a bump in a cavity making no contact with the walls of the cavity even though the secondary surface is fully seated against the cut surface and the joint is under load.

In some cases, the bump and cavity can be sized and shaped relative to one another such that when the secondary surface is fully seated against the cut surface and the joint is under load, the spacer is free to rotate on the cut surface about a non-lateral axis, as shown in FIG. 8. The amount of rotation allowed is limited to less than a maximum. The maximum allowed rotation of the spacer relative to the bone could be as high as 5 degrees or as low as 0.2 degrees, or any value in between.

In some cases, the secondary surface conform to the cut surface of the first bone such that, when the secondary surface is fully seated against the cut surface, a portion of the secondary surface is at least 200 microns from a facing portion of the cut surface of the first bone, even when the joint is under load. This distance allows for some bone growth on the cut surface.

A method for placing a joint replacement spacer may include (1) distracting a joint that comprises a first bone having a first articular surface and a second bone having a second articular surface; (2) preparing the first bone by removing the first articular surface of the first bone, thereby creating a cut surface on the first bone, and forming a cavity in the first bone; wherein the cavity opens onto the cut surface;

(3) placing a spacer against the cut surface of the first bone, the spacer having (a) a primary surface sized and shaped to articulate with the second articular surface of the second bone; (b) a secondary surface conforming to the cut surface of the first bone, so that the spacer tends to remain fully seated against the cut surface while remaining free to move on the cut surface; and (c) a bump protruding from the secondary surface at a location such that, when the secondary surface is fully seated against the cut surface, the bump extends into the cavity, without laterally filling the cavity, thereby leaving the spacer free to move on the cut surface to the extent that the bump can move laterally within the cavity, even when the joint is under load; and (4) reapproximating the joint such that the primary surface of the spacer articulates with the second articular surface of the second bone, and the secondary surface of the spacer fully seats against the cut surface of the first bone.

The bump may be sized and shaped so that, when the secondary surface is fully seated against the cut surface, the bump extends into the cavity, without laterally filling the cavity, thereby leaving the spacer free to move in any direction on the cut surface to the extent that the bump can move laterally within the cavity, even when the joint is under load.

The bump may be sized and shaped so that, when the secondary surface is fully seated against the cut surface, the bump extends into the cavity, without laterally filling the cavity, thereby leaving the spacer free both to rotate and translate simultaneously on the cut surface to the extent that the bump can move laterally within the cavity, even when the joint is under load. In some embodiments, the bump is provided with exactly two degrees of freedom in translation (no more, no less) and exactly one degree of freedom in rotation (no more, no less).

The bump may be sized and shaped so that, when the secondary surface is fully seated against the cut surface, the bump extends into the cavity, without laterally filling the cavity, thereby leaving the spacer free to move in at least two axial directions on the cut surface to the extent that the bump can move laterally within the cavity, even when the joint is under load.

The invention claimed is:

1. A method comprising:
    distracting a joint that comprises a first bone having a first articular surface and a second bone having a second articular surface;
    preparing the first bone by:
        removing the first articular surface of the first bone, thereby creating a cut surface on the first bone; and
        forming a cavity in the first bone;
        wherein the cavity opens onto the cut surface;
    placing a spacer against the cut surface of the first bone, the spacer having:
        a primary surface sized and shaped to articulate with the second articular surface of the second bone;
        a secondary surface conforming to the cut surface of the first bone, so that the spacer tends to remain fully seated against the cut surface while remaining free to move on the cut surface; and
        a bump protruding from the secondary surface at a location such that, when the secondary surface is fully seated against the cut surface, the bump extends into the cavity, without laterally filling the cavity, thereby leaving the spacer free to move in any direction on the cut surface to the extent that the bump can move laterally within the cavity, even when the joint is under load; and
    reapproximating the joint such that the primary surface of the spacer articulates with the second articular surface of the second bone, and the secondary surface of the spacer fully seats against the cut surface of the first bone.

2. The method of claim 1 wherein the spacer comprises pyrolytic carbon.

3. The method of claim 2, wherein all surfaces of the spacer are formed entirely from pyrolytic carbon.

4. The method of claim 1, wherein the cavity is formed in the cut surface after the cut surface is created in its entirety.

5. The method of claim 1 wherein preparing the first bone comprises removing the first articular surface of the first bone and forming the cavity simultaneously.

6. The method of claim 1, wherein preparing the first bone comprises forming the cavity before removing the first articular surface of the first bone.

7. The method of claim 1, wherein preparing the first bone comprises forming the cavity after removing the first articular surface of the first bone.

8. The method of claim 1 wherein the secondary surface comprises a planar portion.

9. The method of claim 8 wherein the secondary surface comprises two non-parallel planar portions.

10. The method of claim 1 wherein the secondary surface comprises a cylindrical portion.

11. The method of claim 1 wherein the secondary surface comprises a spheroidal portion.

12. The method of claim 1 wherein the secondary surface comprises a ellipsoidal portion.

13. The method of claim 1 wherein, when the secondary surface is fully seated against the cut surface, the bump can translate within the cavity in any lateral direction.

14. The method of claim 13 wherein a lateral cross-section of the bump defines a first shape, a lateral cross-section of the cavity defines a second shape, and the first and second shapes are geometrically similar.

15. The method of claim 13 wherein the bump and cavity are sized and shaped relative to one another such that, when the secondary surface is fully seated against the cut surface, the spacer is not permitted to move off the secondary surface.

16. The method of claim 1 wherein, when the secondary surface is fully seated against the cut surface, the bump can translate within the cavity in only one lateral direction.

17. The method of claim 1 wherein, when (a) the secondary surface is fully seated against the cut surface, and (b) the joint is under load, the bump can translate within the cavity in any lateral direction.

18. The method of claim 1 wherein the secondary surface and the cut surface are sized and shaped relative to one another such that, when the secondary surface is fully seated against the cut surface, the movement of the spacer on the secondary surface is limited in a first direction by the engagement of the secondary surface with the cut surface.

19. The method of claim 18 wherein, when the secondary surface is fully seated against the cut surface, the bump is allowed to translate within the cavity in a second direction that is both (a) lateral, and (b) different from the first direction.

20. The method of claim 1 wherein the bump and the cavity are sized and shaped relative to one another such that, when the secondary surface is fully seated against the cut surface and the joint is under load, the cavity and bump do not contact one another in at least one relative position.

21. The method of claim 1 wherein the bump and the cavity are sized and shaped relative to one another such that, when the secondary surface is fully seated against the cut surface, the spacer is free to rotate on the cut surface, even when the joint is under load, wherein (a) the rotation is about a non-lateral axis, and (b) the maximum allowed rotation is in the range of 0.2 degrees to 5 degrees.

22. The method of claim 1 wherein the secondary surface conforms to the cut surface of the first bone such that, when the secondary surface is fully seated against the cut surface, a portion of the secondary surface is at least 200 microns from a facing portion of the cut surface of the first bone, even when the joint is under load.

23. The method of claim 1 wherein:
preparing the first bone further comprises forming a second cavity that also opens onto the cut surface; and
the spacer further comprises a second bump protruding from the secondary surface at a location such that, when the secondary surface is fully seated against the cut surface, the second bump extends into the second cavity, without laterally filling the second cavity, thereby leaving the spacer free to move in any direction on the cut surface to the extent that the second bump can move laterally within the second cavity, even when the joint is under load.

24. A method comprising:
distracting a joint that comprises a first bone having a first articular surface and a second bone having a second articular surface;
preparing the first bone by:
  removing the first articular surface of the first bone, thereby creating a cut surface on the first bone; and
  forming a cavity in the first bone;
  wherein the cavity opens onto the cut surface;
preparing the second bone by removing the second articular surface so as to create a prepared articular surface on the second bone;
placing a spacer against the cut surface of the first bone, the spacer having:
  a primary surface sized and shaped to articulate with the prepared articular surface of the second bone;
  a secondary surface conforming to the cut surface of the first bone, so that the spacer tends to remain fully seated against the cut surface while remaining free to move on the cut surface; and
  a bump protruding from the secondary surface at a location such that, when the secondary surface is fully seated against the cut surface, the bump extends into the cavity, without laterally filling the cavity, thereby leaving the spacer free both to rotate and translate simultaneously on the cut surface to the extent that the bump can move laterally within the cavity, even when the joint is under load; and
reapproximating the joint such that the primary surface of the spacer articulates with the prepared articular surface of the second bone, and the secondary surface of the spacer fully seats against the cut surface of the first bone.

* * * * *